United States Patent [19]

Kanda et al.

[11] Patent Number: 5,068,349

[45] Date of Patent: Nov. 26, 1991

[54] MITOMYCIN DERIVATIVES

[75] Inventors: Yutaka Kanda, Houston, Tex.; Masaji Kasai, Fujisawa, Japan; Hitoshi Arai; Makoto Morimoto, both of Shizuoka, Japan; Tadashi Ashizawa, Numazu, Japan

[73] Assignee: Kyowa Hakko Kogyo Co., Ltd., Tokyo, Japan

[21] Appl. No.: 404,353

[22] Filed: Sep. 7, 1989

[30] Foreign Application Priority Data

Sep. 9, 1988 [JP] Japan .................... 63-224484

[51] Int. Cl.$^5$ .................... C07D 487/14; A61K 31/40
[52] U.S. Cl. ........................ 548/418; 548/422
[58] Field of Search ............. 548/418, 422; 514/410

[56] References Cited

U.S. PATENT DOCUMENTS 4,880,825 11/1989 Kasai et al. ............... 548/422
4,927,943 5/1990 Vyas et al. ............... 548/422

FOREIGN PATENT DOCUMENTS 0284380 9/1988 European Pat. Off. .
0307179 3/1989 European Pat. Off. .

OTHER PUBLICATIONS

Chemical Abstracts, vol. 113, 131886t (1990).
Patent Abstracts of Japan, vol. 3, No. 142 (C-65)(161), Nov. 24, 1979; & JPA 54-122797 (Kyowa Hakko Kogyo K.K.), Sep. 22, 1979 (Cat. D).
Patent Abstracts of Japan, vol. 4, No. 178 (C-14)(26), Jun. 11, 1980; & JPA 55-45322 (Kyowa Hakko Kogyo K.K.), Mar. 31, 1980 (Cat. D).
Patent Abstracts of Japan, vol. 4, No. 178 (C-34)(660), Dec. 10, 1980; & JPA-55-118396 (Kyowa Hakko Kogyo K.K.), Sep. 11, 1980 (Cat. D).

*Primary Examiner*—Nicholas S. Rizzo
*Attorney, Agent, or Firm*—Antonelli, Terry, Stout & Kraus

[57] ABSTRACT

Novel mitomycin derivatives are characterized by a substituent on the $C_6$-methyl group. The mitomycin derivatives exhibit anti-tumor and antibacterial activity and have low toxicity.

3 Claims, No Drawings

MITOMYCIN DERIVATIVES

BACKGROUND OF THE INVENTION

The present invention relates to novel mitomycin derivatives having anti-tumor and antibacterial activity.

Mitomycins are generally known to be antibiotics having antibacterial and anti-tumor activity. From natural sources, mitomycin C is mainly obtained and as trace components, mitomycin A, mitomycin B and porfiromycin (these are described in Merck Index, 10th edition) are obtained. Further, as trace components, there are also known mitomycins D and E (Japanese Published Unexamined Patent Application No. 122797/1979), mitomycins F and J (Japanese Published Unexamined Patent Application No. 45322/1980), mitomycins G, H and K (Japanese Published Unexamined Patent Application No. 118396/1980), and the like. Structures of these mitomycins obtained from natural sources are shown in Table 1.

TABLE 1

Structures of mitomycins obtained from natural sources

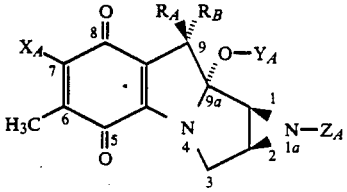

| Mitomycin | $X_A$ | $Y_A$ | $Z_A$ | $R_A$ | $R_B$ |
|---|---|---|---|---|---|
| A | $OCH_3$ | $CH_3$ | H | $CH_2OCONH_2$ | H |
| B | $OCH_3$ | H | $CH_3$ | H | $CH_2OCONH_2$ |
| C | $NH_2$ | $CH_3$ | H | $CH_2OCONH_2$ | H |
| D | $NH_2$ | H | $CH_3$ | H | $CH_2OCONH_2$ |
| E | $NH_2$ | $CH_3$ | $CH_3$ | H | $CH_2OCONH_2$ |
| F | $OCH_3$ | $CH_3$ | $CH_3$ | $CH_2OCONH_2$ | H |
| G | $NH_2$ | $CH_3$ | $CH_3$ | Combined together to form $=CH_2$ | |
| H | $OCH_3$ | H | $CH_3$ | Combined together to form $=CH_2$ | |
| J | $OCH_3$ | $CH_3$ | $CH_3$ | H | $CH_2OCONH_2$ |
| K | $OCH_3$ | $CH_3$ | $CH_3$ | Combined together to form $=CH_2$ | |
| Porfiromycin | $NH_2$ | $CH_3$ | $CH_3$ | $CH_2OCONH_2$ | H |

Some of the above mitomycins show an excellent anti-tumor activity, but they have also serious side effects such as decrease in leucocytes, etc. In view of such background, many derivatives have been synthesized to enhance the activity or to alleviate the toxicity Concerning compounds wherein the $C_6$-methyl group is modified and which are relevant to the present invention, an application directed to mitomycin derivatives of general formula (I) later described wherein W is deuterium ($^2H$) or tritium ($^3H$) was filed by the present applicant [Japanese Patent Application No. 227094/1987 (Japanese Published Unexamined Patent Application No. 70490/1989)].

SUMMARY OF THE INVENTION

An object of the present invention is to provide novel mitomycin derivatives having a substituent on the $C_6$-methyl group which exhibit anti-tumor and antibacterial activity.

The present invention relates to mitomycin derivatives represented by formula (I):

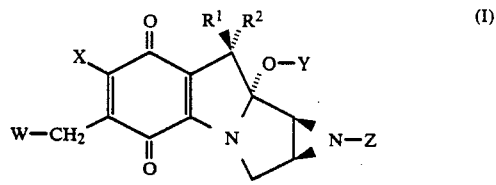

wherein W represents RO or RS (wherein R represents hydrogen, optionally substituted alkyl having 1 to 12 carbon atoms, optionally substituted alkenyl having 2 to 12 carbon atoms, optionally substituted aralkyl or optionally substituted aryl); X represents methoxy or amino; or W and X are combined together to form —S(CH$_2$)$_2$NH— or

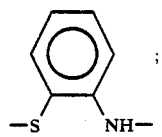

Y represents hydrogen or methyl; Z represents hydrogen, methyl or acyl; and one of $R^1$ and $R^2$ represents carbamoyloxymethyl and the other represents hydrogen, or $R^1$ and $R^2$ are combined together to form methylene (=CH$_2$) [hereinafter referred to as Compounds (I); the same shall apply to compounds represented by formulae with other numbers].

In the definition of R in formula (I), the alkyl having 1 to 12 carbon atoms is a straight-chain or branched alkyl group such as methyl, ethyl, propyl, isopropyl, butyl, isobutyl, tert-butyl, pentyl, hexyl, heptyl, octyl, decyl or dodecyl, which may be substituted with 1 or 2 substituents which may be the same or different. Examples of the substituents include hydroxy; a lower alkoxy having 1 to 4 carbon atoms such as methoxy, ethoxy, propoxy or butoxy; a lower alkoxycarbonyl having 2 to 5 carbon atoms such as methoxycarbonyl, ethoxycarbonyl, propoxycarbonyl or tert-butoxycarbonyl; an acylamino; an acyloxy; a halogen such as fluorine, chlorine, bromine or iodine; an alicyclic alkyl having 3 to 6 carbon atoms such as cyclopropyl, cyclopentyl or cyclohexyl, etc.

The alkenyl having 2 to 12 carbon atoms includes vinyl, allyl, homoallyl, crotyl, cis-7-dodecenyl, etc., which may be substituted with one or two substituents which may be the same or different. Examples of the substituents include hydroxy, a lower alkoxy, a lower alkoxycarbonyl, a halogen, etc. which are the same as defined for the substituents for the alkyl.

The aralkyl means benzyl, phenethyl, benzhydryl, etc. and the aryl means phenyl, naphthyl, etc. The aromatic ring in the aralkyl and the aryl may be substituted with one to three substituents which may be the same or different. Examples of the substituents include hydroxy, a lower alkoxy, a lower alkoxycarbonyl, an acylamino, an acyloxy and a halogen, which are the same as defined for the substituents for the alkyl, nitro, and a lower alkyl having 1 to 4 carbon atoms such as methyl, ethyl, propyl, isopropyl, butyl, isobutyl or tert-butyl.

The acyl in the definition of Z and the acyl in the acylamino and acyloxy in the definition of R include a lower alkanoyl having 1 to 4 carbon atoms such as formyl, acetyl, propionyl or butyryl, and an aroyl such as benzoyl, toluoyl, p-nitrobenzoyl or naphthoyl.

The process for preparing Compounds (I) is described below.

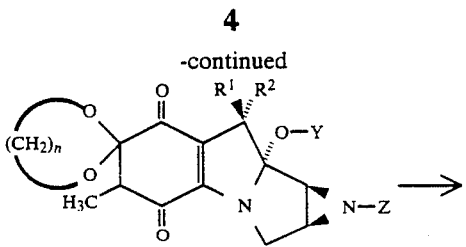

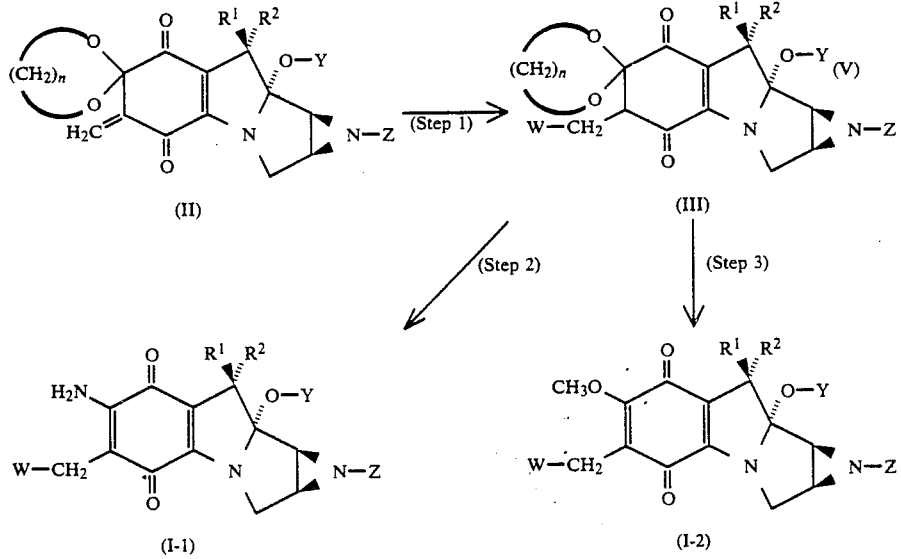

In the formulae, n represents an integer of 2 or 3; and W, Y, Z, R¹ and R² have the same significances as defined above.

STEP 1

Compounds (III) can be prepared by subjecting Compounds (II) to reaction with an alcohol (ROH) or a thiol (RSH) (wherein R has the same significance as defined above) in a solvent inert to the reaction, if necessary, in the presence of a base.

As the solvent, ether, tetrahydrofuran, methylene chloride, chloroform, etc. may be used singly or in combination. In the reaction with the alcohol, the alcohol as a reactant may also be used as a solvent. Further, in the reaction with the alcohol, a base may be added to the reaction system. As the base, tetrabutyl ammonium hydroxide, benzyl trimethyl ammonium hydroxide, etc. are preferably used in a catalytic amount.

The reaction is usually completed in a temperature range of 0° to 30° C. in 10 minutes to 2 days.

Compounds (II) which are starting materials can be prepared by the following reaction steps.

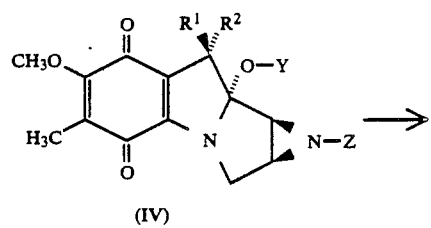

In the formulae, Y, Z, R¹ and R² have the same significances as defined above.

First, mitomycins (IV) having methoxy group at the 7-position (for example, those shown in Table 1) are allowed to react with ethylene glycol or 1,3-propanediol in the presence of a base to give Compounds (V) [Japanese Patent Application No. 69073/1988 (Japanese Published Unexamined Patent Application No. 6275/1989)].

Next, Compounds (V) are allowed to react with a seleneylating agent such as phenylselenenyl halide to give Compounds (VI). Compounds (VI) are oxidized with an oxidizing agent such as metachloroperbenzoic acid to give Compounds (II) [Japanese Patent Application No. 227094/1987 (Japanese Published Unexamined Patent Application No. 70490/1989)].

Compounds (III) can also be prepared directly from Compounds (VI) and the alcohol or thiol under the conditions similar to those described above.

STEP 2

Compounds (I-1) [Compounds (I) wherein X is amino] can be prepared by subjecting Compounds (III) obtained in Step 1 to reaction with an equivalent amount to a large excess of ammonia or ammonium acetate in an inert solvent. Any solvent is usable so long as it can dissolve Compounds (III). For example, alcohols such as methanol and ethanol; ethers such as diethyl ether and tetrahydrofuran; halogenated hydrocarbons such as methylene chloride and chloroform; acetonitrile, dimethylformamide, dimethylsulfoxide, etc. may be used singly or in combination. The reaction is usually completed in a temperature range of 0° to 30° C. in one hour to 7 days.

STEP 3

Compounds (I-2) [Compounds (I) wherein X is methoxy] can be prepared by subjecting Compounds (III) to reaction in methanol in the presence of a base. As the base used for the reaction, there may be mentioned $R^3OM$ (wherein $R^3$ represents a lower alkyl having 1 to 4 carbon atoms such as methyl, ethyl, butyl or tert-butyl; and M represents an alkali metal such as lithium, sodium or potassium or an alkaline earth metal such as calcium or magnesium); hydroxides, carbonates or bicarbonates of the same alkali metals or alkaline earth metals as described above; tertiary organic amines such as triethylamine, tributylamine and N-methylmorpholine; quaternary ammonium hydroxides such as tetrabutyl ammonium hydroxide, etc. An amount of the base is in the range of 0.001 to 10 equivalents, preferably 0.01 to 3 equivalents, based on Compound (III). The reaction is usually completed in a temperature range of 20° to 30° C. in 2 to 24 hours.

When Compounds (III) wherein Z is acyl are used in Steps 2 and 3, deacylation sometimes occurs simultaneously under the reaction conditions described above to give the corresponding Compounds (I-1) and (I-2) wherein Z is hydrogen, respectively.

Compounds (I) wherein W and X are combined together to form $—S(CH_2)_2NH—$ or

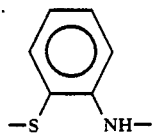

can be prepared by subjecting Compounds (II) to reaction with the corresponding 2-aminoethanethiol or 2-aminothiophenol or hydrochlorides thereof in a similar manner as in Step 1. When the thiol hydrochlorides are used, it is preferred to add organic bases such as pyridine and triethylamine in an equivalent amount or more.

Compounds (I) wherein W is hydroxy can also be prepared by treating Compounds (III) wherein W is 3,4-dimethoxybenzyloxy group with a suitable oxidizing agent, for example, 2,3-dichloro-5,6-dicyano-1,4-benzoquinone (DDQ), and subjecting the resulting Compounds (III) wherein W is hydroxy to Step 2 or 3. As the solvent used for the oxidation, a solvent mixture of water and a water-immiscible solvent such as methylene chloride or chloroform is preferred. The reaction is usually completed in a temperature range of 0° to 30° C. in 2 to 12 hours.

Further, Compounds (I) wherein Z is hydrogen can also be prepared by hydrolysis (deacylation) of the corresponding Compounds (I) wherein Z is protected with an acyl such as acetyl under basic conditions. As the base, amines such as ammonia, inorganic bases such as sodium bicarbonate, sodium hydroxide and potassium hydroxide, etc. can be used. It is preferred to use methanol, water, etc. as the solvent. The reaction is usually completed in 1 to 20 hours.

Post-treatments in the respective steps for producing the intermediates and the desired compounds described above are carried out in the following manner. The reaction solution is concentrated as it is or, if necessary, after neutralization, and then purified. Alternatively, after being neutralized if necessary, the reaction solution is extracted with a water-immiscible solvent such as chloroform, methylene chloride or ethyl acetate, and the extract is washed with water, aqueous sodium chloride solution, etc., and then concentrated, followed by purification. Purification is effected by column chromatography using silica gel, etc. or thin layer chromatography (TLC) or by recrystallization, etc. In the case of the intermediates, they may be directly subjected to the subsequent reaction without any particular purification.

Examples of Compounds (I) obtained by the process described above are shown in Table 2.

TABLE 2

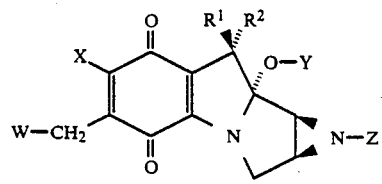

| Compound (Example) | W | X | Y | Z | $R^1$ | $R^2$ |
|---|---|---|---|---|---|---|
| 1(1) | $OCH_3$ | $NH_2$ | $CH_3$ | $CH_3$ | $CH_2OCONH_2$ | H |
| 2(2) | $OCH_3$ | $NH_2$ | $CH_3$ | H | $CH_2OCONH_2$ | H |
| 3(3) | $OCH_3$ | $NH_2$ | H | $CH_3$ | H | $CH_2OCONH_2$ |
| 4(4) | $OCH_3$ | $OCH_3$ | $CH_3$ | H | $CH_2OCONH_2$ | H |
| 5(4) | $OCH_3$ | $OCH_3$ | $CH_3$ | $COCH_3$ | $CH_2OCONH_2$ | H |
| 6(5) | $O(CH_2)_3CH_3$ | $NH_2$ | $CH_3$ | H | $CH_2OCONH_2$ | H |
| 7(6) | 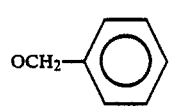 | $NH_2$ | $CH_3$ | H | $CH_2OCONH_2$ | H |
| 8(7) | $OCH(CH_3)_2$ | $NH_2$ | $CH_3$ | H | $CH_2OCONH_2$ | H |

TABLE 2-continued

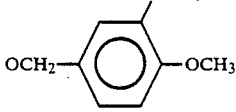

| Compound (Example) | W | X | Y | Z | R¹ | R² |
|---|---|---|---|---|---|---|
| 9(8) | (3,4-dimethoxy-benzyl: OCH₃, OCH₃, OCH₂—) | $NH_2$ | $CH_3$ | H | $CH_2OCONH_2$ | H |
| 10(9) | OH | $NH_2$ | $CH_3$ | H | $CH_2OCONH_2$ | H |
| 11(10) | $SC_2H_5$ | $NH_2$ | $CH_3$ | H | $CH_2OCONH_2$ | H |
| 12(11) | $S(CH_2)_2CO_2CH_3$ | $NH_2$ | $CH_3$ | H | $CH_2OCONH_2$ | H |
| 13(12) | $S(CH_2)_2OH$ | $NH_2$ | $CH_3$ | H | $CH_2OCONH_2$ | H |
| 14(13) | $S(CH_2)_{11}CH_3$ | $NH_2$ | $CH_3$ | H | $CH_2OCONH_2$ | H |
| 15(14) | $SCH_2CH(OH)CH_2OH$ | $NH_2$ | $CH_3$ | H | $CH_2OCONH_2$ | H |
| 16(15) | $SCH(CH_3)_2$ | $NH_2$ | $CH_3$ | H | $CH_2OCONH_2$ | H |
| 17(16) | S-phenyl | $NH_2$ | $CH_3$ | H | $CH_2OCONH_2$ | H |
| 18(17) | $SCH_2$-phenyl | $NH_2$ | $CH_3$ | H | $CH_2OCONH_2$ | H |
| 19(18) | $S(CH_2)_2NH$ | | $CH_3$ | $COCH_3$ | $CH_2OCONH_2$ | H |
| 20(19) | $S(CH_2)_2NH$ | | $CH_3$ | H | $CH_2OCONH_2$ | H |
| 21(20) | $OCH_2CH=CH_2$ | $NH_2$ | $CH_3$ | H | $CH_2OCONH_2$ | H |
| 22(21) | $OCH_2CH_2OCH_3$ | $NH_2$ | $CH_3$ | H | $CH_2OCONH_2$ | H |
| 23(22) | S-(4-hydroxyphenyl) | $NH_2$ | $CH_3$ | H | $CH_2OCONH_2$ | H |
| 24(23) | S-(4-chlorophenyl) | $NH_2$ | $CH_3$ | H | $CH_2OCONH_2$ | H |
| 25(24) | S-(4-methoxyphenyl) | $NH_2$ | $CH_3$ | H | $CH_2OCONH_2$ | H |
| 26(25) | S-(4-nitrophenyl) | $NH_2$ | $CH_3$ | H | $CH_2OCONH_2$ | H |
| 27(26) | S-(2-aminophenyl) | | $CH_3$ | $COCH_3$ | $CH_2OCONH_2$ | H |

TABLE 2-continued

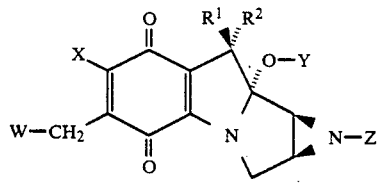

| Compound (Example) | W | X | Y | Z | R¹ | R² |
|---|---|---|---|---|---|---|
| 28(27) | [benzothiazole-S-CH₂-] | | CH₃ | H | CH₂OCONH₂ | H |
| 29(28) | SCH₂-cyclopropyl | NH₂ | CH₃ | H | CH₂OCONH₂ | H |

The antibacterial activity and anti-tumor activity of representative Compounds (I) are specifically shown below by referring to experimental examples.

EXPERIMENTAL EXAMPLE 1

The antibacterial activity of Compounds (I) against various bacteria [minimum growth inhibitory concentration ($\mu$ g/ml)] is shown in Table 3.

The minimum growth inhibitory concentration was determined by the agar dilution method at pH 7.0. In the table, names of bacteria are shown by the following symbols.

SF : *Streptococcus faecium* ATCC 10541
SA : *Staphylococcus aureus* ATCC 6538P
PV : *Proteus vulgaris* ATCC 6897
KP : *Klebsiella pneumoniae* ATCC 10031

TABLE 3

| Compound | SF | SA | PV | KP |
|---|---|---|---|---|
| 1 | 0.63 | 0.31 | >40 | 0.63 |
| 2 | 1.3 | 1.3 | 1.3 | 0.31 |
| 4 | 10 | 10 | 2.5 | 0.63 |
| 6 | 0.31 | 0.63 | — | 5.0 |
| 7 | 0.16 | 0.63 | — | 5.0 |
| 8 | 0.31 | 0.63 | 40 | 0.63 |
| 10 | 10 | 5.0 | 5.0 | 1.3 |
| 11 | 0.31 | 0.039 | 0.16 | 1.3 |
| 12 | 0.63 | 0.31 | 1.3 | 0.31 |
| 13 | 10 | 10 | 40 | 5.0 |
| 14 | 0.39 | 0.20 | >50 | — |
| 16 | 0.078 | 0.16 | 10 | 1.3 |
| 17 | 0.31 | 20 | 40 | 10 |
| 18 | 0.039 | 0.16 | 40 | 5.0 |
| 20 | 5.0 | 2.5 | 40 | 10 |

EXPERIMENTAL EXAMPLE 2

The effect of representative Compounds (I) against Sarcoma 180 solid tumor is shown in Table 4.

$LD_{50}$ and $ED_{50}$ were determined by the following methods, respectively.

(1) Determination of $LD_{50}$

Five ddY mice were used for each group, and the test compounds were administered once to the mice intraperitoneally or intravenously. After the administration, the mice were observed for 14 days and deaths were noted. $LD_{50}$ was calculated from the death rate of each group according to the Behrens Kaerber's method.

(2) Determination of $ED_{50}$

Sarcoma 180 cells ($5 \times 10^6$ cells) were implanted intraperitoneally into a ddY mouse and the cells were collected from the ascitic fluid of the animal 7 days after the implantation. The cells were washed once with sterilized physiological saline solution and then suspended in sterilized physiological saline solution to prepare a cell suspension containing $5 \times 10^7$ cells/ml. The suspension (0.1 ml) was subcutaneously implanted into the right axilla of male ddY mice weighing $20 \pm 2$ g.

A test compound was dissolved in physiological saline solution or Tween 80-containing physiological saline solution, and 0.1 to 0.2 ml of the solution was administered to 5 mice as one group intraperitoneally or intravenously 24 hours after the implantation of the tumor cells.

The anti-tumor activity of the test compound was determined by measuring the major axis (a) and the minor axis (b) of the tumor 7 days after the implantation, calculating a value of $(a) \times (b)^2/2$ corresponding to the volume of the tumor, and calculating a ratio T/C of the volume (T) of the group which received the test compound to the volume (C) of the control group which received no test compound T/C at each dose given was plotted on a graph in which T/C is shown by an ordinary scale on the vertical axis and a dose is shown by a logarithmic scale on the abscissa. The relationship between the dose and T/C was determined to be a straight line by the least-squares method. According to the regression equation of the straight line obtained, a dose at which T/C showed 0.5 was calculated as $ED_{50}$.

TABLE 4

| Compound | $LD_{50}$ (mg/kg) | $ED_{50}$ (mg/kg) | Route for Administration |
|---|---|---|---|
| 2 | 75 | 34.0 | intraperitoneal |
| 6 | >50 | 38.0 | intraperitoneal |
| 7 | 60 | 25.2 | intraperitoneal |
| 8 | >50 | 14.9 | intravenous |
| 11 | 30 | 11.6 | intraperitoneal |
| 16 | 37.5 | 8.4 | intravenous |
| 17 | 50 | 6.1 | intravenous |
| 18 | 56.6 | 20.2 | intravenous |
| 20 | 22.5 | 12.6 | intravenous |

The compounds obtained by the present invention are useful as anti-tumor agents. The compounds can be used as they are, or in various forms for administration. For example, when Compounds (I) are used in the form of an injection, they are dissolved in a diluent which is conventionally used in the art such as physiological saline solution or glucose, lactose or mannitol solution for injection. Alternatively, the compounds may be freeze-dried according to the Japanese Pharmacopoeia or may be prepared into injectable powder by adding sodium chloride thereto. In addition, the injection may also contain an auxiliary agent such as polyethylene glycol or HCO-60 (surfactant, manufactured by Nikko Chemical Co., Ltd.), ethanol and/or a carrier such as liposome or cyclodextrin. These injections are generally intravenously administered, but may also be administered intra-arterially, intraperitoneally or intrathoracically.

Compounds (I) may also be formed into tablets, granules, powder or syrup for oral administration with an appropriate excipient, disintegrator, binder or lubricant in a conventional manner. Further, Compounds (I) may be mixed with a conventionally used carrier and formed into suppositories for rectal administration in a conventional manner.

Dosage may appropriately vary according to the administration schedule, the kind of Compounds (I), and the age and condition of a patient. Administration schedule may also be varied according to the condition of a patient and the dosage. For example, the compounds can be intermittently administered in a dose of 0.06 to 6 mg/kg once a week or once every three weeks.

Certain embodiments of the invention are illustrated in the following examples.

Physicochemical data of each compound were obtained by using the following devices.

NMR : Bruker AM-400 (400 MHz),
Nippon Denshi JNM-GX 270 (270 MHz),
Nippon Denshi PS-100 (100 MHz) or VARIAN EM 390 (90 MHz)
MS : Hitachi M-80B (measured by the SI method) or Nippon Denshi JMS-D300 (measured by the FAB method)
IR : Nippon Bunko IR-810 (measured by the KBr method)
TLC : silica gel Art 5719 or 5715 (manufactured by Merck Inc.)

EXAMPLE 1

6-Demethyl-6-methoxymethylporfiromycin

Compound 1

7-Demethoxy-6,7-dihydro-7-ethylenedioxy-6-phenyl-selenomitomycin F [Compound (VI): $R^1 = CH_2OCONH_2$, $R^2 = H$, $Y = Z = CH_3$, $n = 2$] (70 mg) was dissolved in 2.5 ml of chloroform, and 0.2 ml of pyridine and 40 mg of m-chloroperbenzoic acid (purity 70%; hereinafter referred to as MCPBA) were added to the solution at 0° C. After stirring for 5 minutes, 0.5 ml of methanol was added to the mixture. The resulting mixture was stirred at room temperature for 8 hours. Then, 0.5 ml of 6.8 M ammonia/methanol solution was added thereto, followed by stirring at room temperature for 14 hours. The reaction mixture was concentrated and the residue was subjected to silica gel column chromatography. Elution was carried out with chloroform:methanol (96:4, v/v), and reddish purple fractions were collected. After the solvent was distilled off under reduced pressure, the residue was further purified by TLC and then powdered with chloroform-n-hexane to give 29 mg (yield 59%) of Compound 1 as gray powder.

TLC : $R_f = 0.49$ (CHCl$_3$:CH$_3$OH = 9:1)
MS (m/z): 379(M$^+$ +1); $C_{17}H_{22}N_4O_6 = 378$
NMR (400 MHz, pyridine-d$_5$)δ:8.02(bs, 2 H), 7.70(b, 2 H), 5.33(dd, J=10.6, 4.4 Hz, 1 H), 4.79(dd, J=10.6 11.6 Hz, 1 H), 4.61(d, J=11.3 Hz, 1 H), 4.57 (d, J=11.6 Hz, 1 H), 4.49(d, J=12.8 Hz, 1 H), 3.98 (dd, J=11.6, 4.4 Hz, 1 H), 3.52(dd, J=13.0, 2.2 Hz, 1 H), 3.21(s, 3 H), 3.17(s, 3 H), 2.53(d, J=4.7 Hz, 1 H), 2.24(s, 3 H), 2.15(dd, J=4.7, 2.0 Hz, 1 H)

EXAMPLE 2

6-Demethyl-6-methoxymethylmitomycin C

Compound 2

1a-Acetyl-7-demethoxy-6,7-dihydro-7-ethylenedioxy-6-phenylselenomitomycin A [Compound (VI):$R^1 = CH_2OCONH_2$, $R^2 = H$, $Y = CH_3$, $Z = COCH_3$, $n = 2$] (297 mg) was dissolved in 10 ml of chloroform and 1.0 ml of pyridine, and 200 mg of MCPBA was added to the solution at 0° C. After stirring at room temperature for 10 minutes, 5.0 ml of methanol was added to the mixture. The resulting mixture was stirred at room temperature for 5 hours. The reaction mixture was poured into an aqueous sodium bicarbonate solution and the mixture was extracted with chloroform. The chloroform layer was washed with saturated aqueous sodium chloride solution and then dried over anhydrous sodium sulfate. After the solvent was distilled off under reduced pressure, the residue was subjected to silica gel column chromatography. Elution was carried out with chloroform:methanol (97:3, v/v), and yellow fractions were collected. The solvent was distilled off under reduced pressure and the residue was dissolved in 1.0 ml of methanol. Then, 0.5 ml of 6.8 M ammonia/methanol solution was added to the solution, followed by stirring at room temperature for 4 hours. After the solvent was distilled off under reduced pressure, the residue was subjected to silica gel column chromatography and eluted with chloroform : methanol (95:5, v/v). Purple fractions were collected, and the solvent was distilled off under reduced pressure to give 53 mg (yield 28%) of Compound 2.

TLC : $R_f = 0.31$ (CHCl$_3$:CH$_3$OH = 9:1)
MS (m/z): 365(M$^+$ +1); $C_{16}H_{20}N_4O_6 = 364$
IR (cm$^{-1}$): 3430, 3325, 2922, 1720, 1597, 1543, 1449, 1399, 1338, 1217, 1057, 925, 854, 811, 763, 705
NMR (400 MHz, CDCl$_3$)δ:6.16(bs, 2 H), 4.82(bs, 2 H),
4.71(dd, J=10.8, 4.4 Hz, 1 H), 4.54(t, J=10.6 Hz, 1 H), 4.44(d, J=12.6 Hz, 1 H), 4.37(d, J=12.6 Hz, 1 H), 4.27(d, J=12.8 Hz, 1 H), 3.64(dd, J=10.4, 4.4 Hz, 1 H), 3.52(dd, J=12.8, 2.0 Hz, 1 H), 3.31 (s, 3 H), 3.22(s, 3 H), 2.90(d, J=4.4 Hz, 1 H), 2.83 (dd, J=4.4, 2.0 Hz, 1 H), 1.25(bs, 1 H)

EXAMPLE 3

6-Demethyl-6-methoxymethylmitomycin D (Compound 3

7-Demethoxy-6,7-dihydro-7-ethylenedioxy-6-phenyl-selenomitomycin B [Compound (VI): $R^1 = Y = H$, $R^2 = CH_2OCONH_2$, $Z = CH_3$, $n = 2$] (368 mg) was dissolved in 20 ml of chloroform and 1.5 ml of pyridine, and 220 mg of MCPBA was added to the solution. After stirring for 30 minutes, 5.0 ml of methanol was added to the mixture. The resulting mixture was stirred at room temperature for 15 hours and 0.5 ml of 6.8 M ammonia/methanol solution was added to the mixture. After three hours, the reaction mixture was poured into an aqueous sodium bicarbonate solution. The organic layer was removed, and the water layer was subjected to column chromatography using HP-20 (Mitsubishi Kasei Corporation). Elution was carried out with water:methanol (1:1, v/v), and purple fractions were collected. The fractions were concentrated and the residue was subjected to silica gel column chromatography and eluted with chloroform : methanol (95:5, v/v). Bluish purple fractions were collected, and the solvent was distilled off under reduced pressure to give 50 mg (yield 20%) of Compound 3.

TLC : $R_f$=0.24 (CHCl$_3$:CH$_3$OH=9:1)

MS (m/z): 367(M$^+$+3), 366(M$^+$+2), 365(M$^+$+1); C$_{16}$H$_{20}$N$_4$O$_6$=364

IR (cm$^{-1}$): 3400, 1705, 1597, 1542, 1445, 1345, 1158, 1070, 933, 846, 817, 707,

NMR (400 MHz, pyridine-d$_5$)δ:8.27(bs, 1 H), 7.79(bs, 2 H), 7.36(bs, 2 H) 5.47(dd, J=10.6, 3.7 Hz, 1 H), 5.19(t, J=10.3 Hz, 1 H), 4.54(d, J=13.0 Hz, 1 H), 4.50(d, J=13.0 Hz, 1 H), 4.42(d, J=13.0 Hz, 1 H), 4.23(dd, J=10.1, 3.4 Hz, 1 H), 3.66(dd, J=13.0, 2.0 Hz, 1 H), 3.16(s, 3 H), 2.45(d, J=4.9 Hz, 1 H), 2.22(dd, J=4.9, 2.0 Hz, 1 H), 2.12(s, 3 H)

EXAMPLE 4

6-Demethyl-6-methoxymethylmitomycin A

Compound 4 and 1a-acetyl-6-demethyl-6-methoxymethylmitomycin A

Compound 5

1a-Acetyl-7-demethoxy-6,7-dihydro-7-ethylenedioxy-6-phenylselenomitomycin A (312 mg) was dissolved in 4 ml of chloroform and 0.5 ml of pyridine, and 274 mg of MCPBA was added to the solution at 0° C. After stirring for one hour, 2 ml of methanol was added to the mixture. The resulting mixture was stirred at room temperature for 3 hours. The reaction mixture was poured into an aqueous sodium bicarbonate solution and the mixture was extracted with chloroform. The chloroform layer was washed with saturated aqueous sodium chloride solution and then dried over anhydrous sodium sulfate. The solvent was distilled off under reduced pressure and the residue was subjected to silica gel column chromatography. Elution was carried out with chloroform:methanol (97:3, v/v), and yellow fractions were collected. After the solvent was distilled off under reduced pressure, the residue was dissolved in 4 ml of methanol and 1 mg of potassium hydroxide was added to the solution. The mixture was stirred at room temperature for 12 hours and then neutralized with dry ice, followed by addition of saturated aqueous sodium chloride solution. The resulting mixture was extracted with chloroform, and the chloroform layer was dried over anhydrous sodium sulfate and concentrated. The residue was subjected to silica gel column chromatography and eluted with chloroform : methanol (95:5, v/v). Reddish purple fractions were collected and treated in a similar manner as in Example 1 to give 21 mg (yield 10%) of powdered Compound 4 and 24 mg (yield 11%) of powdered Compound 5.

Compound 4:

TLC : $R_f$=0.47 (CHCl$_3$:CH$_3$OH=9:1)

MS (m/z): 382(M$^+$+3); C$_{17}$H$_{21}$N$_3$O$_7$=379

IR (cm$^{-1}$) 3450, 2930, 1701, 1640, 1565, 1444, 1400, 324, 1285, 1215, 1064, 990, 855, 801

NMR (400 MHz, CDCl$_3$)δ: 4.74(b, 2 H), 4.74(dd, J=10.8, 4.4 Hz, 1 H), 4.54(t, J=10.6 Hz, 1 H), 4.26(d, J=10.1 Hz, 1 H), 4.21(d, J=10.1 Hz, 1 H), 4.18(s, 3 H), 4.11 (d, J=12.8 Hz, 1 H), 3.63(dd, J=10.3, 4.4 Hz, 1 H), 3.48(dd, J=12.8, 2.0 Hz, 1 H), 3.37(s, 3 H), 3.21 (s, 3 H), 2.90(d, J=4.4 Hz, 1 H), 2.82(dd, J=4.4, 2.0 Hz, 1 H), 1.26(b, 1 H)

Compound 5:

NMR (100 MHz, CDCl$_3$)δ: major peaks, 4.90(b, 2 H), 4.12 (s, 3 H), 3.35(s, 3 H), 3.17(s, 3 H), 2.12(s, 3 H)

EXAMPLE 5

6-Demethyl-6-n-butoxymethylmitomycin C (Compound 6

Compound 6 (65 mg, yield 23%) was obtained from 400 mg of 1a-acetyl-7-demethoxy-6,7-dihydro-7-ethylenedioxy-6-phenylselenomitomycin A, 257 mg of MCPBA and 3.0 ml of n-butanol in a similar manner as in Example 2.

TLC : $R_f$=0.43 (CHCl$_3$:CH$_3$OH=9:1)

MS (m/z): 409(M$^+$+3), 408(M$^+$+2), 407(M$^+$+1); C$_{19}$H$_{26}$N$_4$O$_6$406

IR (cm$^{-1}$): 3340, 1717, 1638, 1596, 1559, 1449, 378, 1335, 1215, 1057, 854, 825, 703

NMR (400 MHz, CDCl$_3$)δ:6.16(bs, 2 H), 4.72(bs, 2 H), 4.70(dd, J=10.8, 4.4 Hz, 1 H), 4.54(b, 1 H), 4.47 (d, J=12.6 Hz, 1 H), 4.40(d, J=12.6 Hz, 1 H), 4.26 (d, J=12.8 Hz, 1 H), 3.63(dd, J=10.8, 4.4 Hz, 1 H), 3.50(bd, J=12.8 Hz, 1 H), 3.41(t, J=6.6 Hz, 2 H), 3.21(s, 3 H), 2.89(b, 1 H), 2.82(b, 1 H), 1.58-1.30 (m, 4 H), 0.91(t, J=7.6 Hz, 3 H), 0.69(b, 1 H)

EXAMPLE 6

6-Demethyl-6-benzyloxymethylmitomycin C (Compound 7

Compound 7 (32 mg, yield 27%) was obtained from 150 mg of 1a-acetyl-7-demethoxy-6,7-dihydro-7-ethylenedioxy-6-phenylselenomitomycin A, 96 mg of MCPBA and 0.5 ml of benzyl alcohol in a similar manner as in Example 2.

TLC : $R_f$=0.34 (CHCl$_3$:CH$_3$OH=9:1)

MS (m/z): 443(M$^+$+3), 442(M$^+$+2), 441(M$^+$+1); C$_{22}$H$_{24}$N$_4$O$_6$=440

IR (cm$^{-1}$): 3415, 3340, 2916, 1708, 1642, 1595, 1551, 1452, 1404, 1375, 1337, 1207, 1056, 920, 854, 804, 740, 702

NMR (400 MHz, CDCl$_3$)δ:7.37-7.29(m, 5 H), 6.09(bs, 2 H), 4.71(dd, J=10.6, 4.4 Hz, 1 H), 4.65(bs, 2 H), 4.55 (bt, J=10.6 Hz, 1 H), 4.55(d, J=12.6 Hz, 1 H), 4.49 (d, J=12.6 Hz, 1 H), 4.46(s, 2 H), 4.27(d, J=13.0 Hz, 1 H), 3.64(dd, J=10.6, 4.4 Hz, 1 H), 3.52(bd, J=12.3 Hz, 1 H), 3.22(s, 3 H), 2.90(d, J=4.2 Hz, 1 H), 2.82(bd, J=4.2 Hz, 1 H), 0.89(b, 1 H)

EXAMPLE 7

6-Demethyl-6-isopropoxymethylmitomycin C

Compound 8

1a-Acetyl-7-demethoxy-6-demethyl-6,7-dihydro-7-ethylenedioxy-6-methylenemitomycin A [Compound (II): $R^1=CH_2OCONH_2$, $R^2=H$, $Y=CH_3$, $Z=COCH_3$, n=2] (90 mg) was dissolved in 4 ml of isopropyl alcohol and 3 ml of chloroform, and 0.05 ml of Triton B (1% aqueous solution) was added to the solution. After stirring at room temperature for 2 days, the reaction mixture was neutralized with phosphate buffer, pH 4, and extracted with chloroform. The chloroform layer was washed with saturated aqueous sodium chloride solution and then dried over anhydrous sodium sulfate. After the solvent was, distilled off under reduced pressure, the residue was subjected to silica gel column chromatography. Elution was carried out with chloroform:methanol (97:3, v/v), and yellow fractions were collected. The solvent was distilled off under reduced pressure to give 53 mg (yield 52%) of la-acetyl-6-demethyl-6,7-dihydro-7-ethylenedioxy-6-isopropoxymethylmitomycin A [Compound (III): $R^1=CH_2OCONH_2$, $R^2=H$, $W=OCH(CH_3)_2$, $Y=CH_3$, $Z=COCH_3$, n=2].

NMR (90 MHz, $CDCl_3$)δ:major peaks, 4.95(b, 2 H), 3.20,
3.15(s, 3 H), 2.12, 2.09(s, 3 H), 1.00, 0.98(d, J=6 Hz, 6 H)

The above compound was dissolved in 3 ml of methanol, and 0.3 ml of 6.8 M ammonia/methanol solution was added to the solution, followed by stirring at 0° C. for 16 hours. The solvent was distilled off under reduced pressure and the residue was subjected to silica gel column chromatography. Elution was carried out with chloroform:methanol (95:5, v/v), and purple fractions were collected. After the solvent was distilled off under reduced pressure, the residue was dissolved in a small quantity of chloroform, and n-hexane was added to the solution to give powder. Then, the solvent was distilled off under reduced pressure. The residue was thoroughly dried in vacuo at room temperature to give 26 mg (yield 60%) of Compound 8 as gray powder.

TLC $R_f$=0.36 ($CHCl_3$ $CH_3OH$=9:1)
MS (m/z): 394($M^+$+2); $C_{18}H_{24}N_4O_6$=392
IR ($cm^{-1}$): 3288, 2968, 1721, 1647, 1592, 1561, 1441, 1404, 1369, 1265, 1218, 1166, 1121, 950, 924, 853, 822, 763, 702
NMR (400 MHz, $CDCl_3$)δ:6.19(b, 2 H), 4.78(b, 2 H), 4.70(dd, J=10.6, 4.4 Hz, 1 H), 4.51(bt, 1 H), 4.49 (d, J=12.6 Hz, 1 H), 4.40(d, J=12.3 Hz, 1 H), 4.26 (d, J=13.0 Hz, 1 H), 3.65–3.59(m, 1 H), 3.62(dd, J=10.6,
4.4 Hz, 1 H), 3.51(bd, J=13.0 Hz, 1 H), 3.21 (s, 3 H), 2.90(b, 1 H), 2.82(b, 1 H), 1.18(d, J=5.9 Hz, 3 H), 1.17(d, J=6.2 Hz, 3 H), 0.64(b, 1 H)

EXAMPLE 8

6-Demethyl-6-(3,4-dimethoxybenzyloxy)methylmitomycin C

Compound 9

Compound 9 (30 mg, yield 8%) was obtained from 435 mg of la-acetyl-7-demethoxy-6,7-dihydro-7-ethylenedioxy-phenylselenomitomycin A, 200 mg of MCPBA and 1.0 ml of 3,4-dimethoxybenzyl alcohol in a similar manner as in Example 2.

TLC : $R_f$=0.41 ($CHCl_3$:$CH_3OH$=9:1)
MS (m/z): 503($M^+$+3), 502($M^+$+2), 501($M^+$+1); $C_{29}H_{28}N_4O_8$=500
IR ($cm^{-1}$): 3440, 3330, 2925, 1708, 1647, 1597, 1551, 1512, 1455, 1337, 1262, 1136, 1054, 920, 852, 806, 755, 701

NMR (400 MHz, $CDCl_3$)δ:6.89(d, J=8.9 Hz, 1 H), 6.86(s,
1 H), 6.83(d, J=8.6 Hz, 1 H), 6.13(b, 2 H), 4.85(b, 2 H), 4.70(dd, J=10.6, 4.4 Hz, 1 H), b 4.52(d, J=12.6 Hz, 1 H), 4.51(t, J=10.6 Hz, 1 H), 4.46(d, J=12.6 Hz, 1 H), 4.39(s, 2 H), 4.26(d, J=12.8 Hz, 1 H), 3.88(s, 3 H), 3.87(s, 3 H), 3.63(dd, J=10.6, 4.4 Hz, 1 H), 3.52(dd, J=12.8, 1.7 Hz, 1 H), 3.21(s, 3 H), 2.90(d, J=4.4 Hz, 1 H), 2.82(dd, J=4.2, 1.7 Hz, 1 H)

EXAMPLE 9

6-Demethyl-6-hydroxymethylmitomycin C

Compound 10 la-Acetyl-7-demethoxy-6-demethyl-6,7-dihydro-7-ethylenedioxy-6-(3,4-dimethoxybenzyloxy)methylmitomycin A

[Compound (III): $R^1=CH_2OCONH_2$, $R^2=H$,

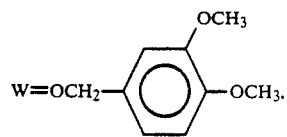

$Y=CH_3$, $Z=COCH_3$, n=2] (110 mg, yield 38%) was obtained from 207 mg of la-acetyl-7-demethoxy-6-demethyl-6,7-dihydro-7-ethylenedioxy-6-methylenemitomycin A, 2.0 ml of 3,4-dimethoxybenzyl alcohol, 0.05 ml of Triton B and 15 ml of chloroform in a similar manner as in Example 7.

The obtained compound (34 mg) was dissolved in 3.0 ml of chloroform, and 0.3 ml of water and 15.8 mg of DDQ were added to the solution at 0° C., followed by stirring at room temperature for 6 hours. After insoluble matters were filtered off, the filtrate was concentrated and the residue was purified by preparative TLC (chloroform:methanol=9:1) to give 10 mg (yield 40%) of la-acetyl-7-demethoxy-6-demethyl-6,7-dihydro-7-ethylenedioxy-6-hydroxy-methylmitomycin A [Compound (III): $R^1=CH_2OCONH_2$, $R^2=H$, $W=OH$, $Y=CH_3$, $Z=COCH_3$, n=2].

Compound 10 (1.2 mg, yield 60%) was obtained from 2.5 mg of the thus obtained compound, 2.0 ml of methanol and 0.3 ml of 6.8 M ammonia/methanol solution in a similar manner as in Example 7.

TLC : R=0.24 ($CHCl_3$:$CH_3OH$=85:15)
MS (m/z): 351($M^+$+1); $C_{15}H_{18}N_4O_6$=350
IR ($cm^{-1}$) 3420, 2930, 1709, 1655, 1600, 1562, 1541, 1450, 1336, 1220, 1063, 973, 857, 825, 764, 700
NMR (400 MHz, pyridine-$d_5$)δ:7.94(b, 2 H), 7.62(b, 2 H),
5.39(dd, J=10.3, 4.2 Hz, 1 H), 5.06(bt, J=11.1 Hz, 1 H), 5.05(d, J=12.5 Hz, 1 H), 5.00(d, J=12.3 Hz, 1 H),
4.50(d, J=12.8 Hz, 1 H), 4.01(dd, J=11.1, 4.2 Hz, 1 H), 3.57(dd, J=12.8, 2.0 Hz, 1 H), 3.18(s, 3 H), 3.13(d, J=4.4 Hz, 1 H), 2.72(dd, J=4.4, 2.0 Hz, 1 H), 1.29(b, 1 H)

EXAMPLE 10

6-Demethyl-6-ethylthiomethylmitomycin C

Compound 11

Compound 11 (39 mg, yield 29%) was obtained from 200 mg of la-acetyl-7-demethoxy-6,7-dihydro-7-ethylenedioxy-6-phenylselenomitomycin A, 128 mg of MCPBA and 0.05 ml of ethanethiol in a similar manner as in Example 2.

TLC : $R_f=0.39$ (CHCl$_3$:CH$_3$OH=9:1)

MS (m/z): 395 (M$^+$+1); C$_{17}$H$_{22}$N$_4$O$_5$S=394

IR (cm$^{-1}$): 3430, 3330, 2920, 1705, 1662, 1600, 1550, 1445, 1338, 1220, 1068, 956, 850, 760, 700

NMR (400 MHz, CDCl$_3$)δ: 5.97(bs, 2 H), 4.76(bs, 2 H), 4.70(dd, J=10.8, 4.4 Hz, 1 H), 4.53(bt, J=10.6 Hz, 1 H), 4.25(d, J=12.8 Hz, 1 H), 3.66(d, J=13.8 Hz, 1 H), 3.63(dd, J=10.1, 4.4 Hz, 1 H), 3.52(d, J=12.8 Hz, 1 H), 3.50(d, J=13.3 Hz, 1 H), 3.22(s, 3 H), 2.90(d, J=4.2 Hz, 1 H), 2.83(bs, 1 H), 2.50(q, J=7.4 Hz, 2 H), 1.27(t, J=7.4 Hz, 3 H), 0.89(b, 1 H)

EXAMPLE 11

6-Demethyl-6-(2-methoxycarbonylethylthio)methylmitomycin C (Compound 12

Compound 12 (66 mg, yield 24%) was obtained from 350 mg of 1a-acetyl-7-demethoxy-6,7-dihydro-7-ethylenedioxy-6-phenylselenomitomycin A, 10 ml of chloroform, 0.5 ml of pyridine, 155 mg of MCPBA and 0.1 ml of methyl 3-mercaptopropionate in a similar manner as in Example 2.

TLC : $R_f=0.29$ (CHCl$_3$CH$_3$OH=9:1)

MS (m/z): 454(M$^+$+2); C$_{19}$H$_{24}$N$_4$O$_7$S=452

IR (cm$^{-1}$): 3415, 2920, 1709, 1597, 1560, 1435, 1339, 1220, 1069, 850, 805, 758, 700

NMR (400 MHz, CDCl$_3$)δ:6.15(b, 2 H), 4.98(b, 2 H), 4.69

(dd, J=10.8, 4.4 Hz, 1 H), 4.49(bt, J=10.3 Hz, 1 H), 4.25(d, J=13.0 Hz, 1H), 3.70(s, 3 H), 3.65(d, J=13.5 Hz, 1 H), 3.62(dd, J=10.3, 4.7 Hz, 1 H), 3.54(d, J=13.0

Hz, 1 H), 3.52(bd, J=12.8 Hz, 1 H), 3.23(s, 3 H), 2.91(bs, 1 H), 2.83(bs, 1 H), 2.76–2.66(m, 4 H), 0.73(b, 1 H)

EXAMPLE 12

6-Demethyl-6-(2-hydroxyethylthio)methylmitomycin C

Compound 13

1a-Acetyl-7-demethoxy-6,7-dihydro-7-ethylenedioxy-6-(2-hydroxyethylthio)methylmitomycin A [Compound (III): R$^1$=CH$_2$OCONH$_2$, R$^2$=H, W=S(CH$_2$)$_2$OH, Y=CH$_3$, Z=COCH$_3$, n=2] (129 mg, yield 60%) was obtained from 273 mg of 1a-acetyl-7-demethoxy-6,7-dihydro-7-ethylenedioxy-6-phenylselenomitomycin A, 6 ml of tetrahydrofuran, 0.5 ml of pyridine, 151 mg of MCPBA and 104 mg of 2-mercaptoethanol in a similar manner as in Example 2.

NMR (90 MHz, CDCl$_3$)δ:major peaks, 5.24(b, 2 H), 3.23, 3.21(s, 3 H), 2.05(s, 3 H)

Compound 13 (64 mg, yield 55%) was obtained as brown powder from the above compound, 10 ml of methanol and 1.0 ml of 6.8 M ammonia/methanol solution in a similar manner as in Example 7.

TLC : $R_f=0.29$ (CHCl$_3$:CH$_3$OH=9:1)

MS (m/z): 411 (M$^+$+1); C$_{17}$H$_{22}$N$_4$O$_6$S=410

IR (cm$^{-1}$) 3450, 2930, 1715, 1655, 1599, 1551, 1434, 1334, 1225, 1065, 860, 806, 760

NMR (400 MHz, pyridine-d$_5$)δ:8.15(b, 2 H), 7.60(b, 2 H), 6.67(b, 1 H), 5.39(dd, J=10.6, 4.2 Hz, 1 H), 5.07

(bt, 1 H), 4.53(d,J=12.8 Hz, 1 H), 4.12(t, J=6.2 Hz, 2 H), 4.08(d, J=12.8 Hz, 1 H), 4.00(dd, J=11.1, 4.2 Hz, 1 H), 3.95(d, J=13.0 Hz, 1 H), 3.58(bd, J=12.6

Hz, 1 H), 3.17(s, 3 H), 3.12(bs, 1 H), 2.92–2.87 (m, 2 H), 2.73(bs, 1 H), 2.07(b, 1 H)

EXAMPLE 13

6-Demethyl-6-dodecylthiomethylmitomycin C

Compound 14

1a-Acetyl-7-demethoxy-6-demethyl-6,7-dihydro-7-ethylenedioxy-6-n-dodecylthiomethylmitomycin A [Compound (III): R$^1$=CH$_2$OCONH$_2$, R$^2$=H, W=S(CH$_2$)$_{11}$CH$_3$, Y=CH$_3$, Z=COCH$_3$, n=2] (200 mg, yield 62%) was obtained from 300 mg of 1a-acetyl-7-demethoxy-6,7-dihydro-7-ethylenedioxy-6-phenylselenomitomycin A, 5.5 ml of chloroform, 0.3 ml of pyridine, 172 mg of MCPBA and 0.7 ml of 1-dodecanethiol in a similar manner as in Example 2.

NMR (100 MHz, CDCl$_3$)δ:major peaks, 5.34(b, 2 H), 3.28

(s, 3 H), 2.12(s, 3 H), 1.6–1.2(m, 20 H), 0.86(t, J=6 Hz, 3 H)

Compound 14 (35 mg, yield 20%) was obtained as reddish purple powder from the above compound, methanol and 1.0 ml of 6.8 M ammonia/methanol solution in a similar manner as in Example 7.

TLC : $R_f=0.51$ (CHCl$_3$:CH$_3$OH=9:1)

MS (m/z): 537 (M$^+$+3); C$_{27}$H$_{42}$N$_4$O$_5$S=534

IR (cm$^{-1}$): 3440, 3322, 2924, 2854, 1729, 1649, 1598, 1555, 1436, 1333, 1220, 1162, 1070, 992, 953, 926, 853, 812, 783, 760, 703

NMR (400 MHz, CDCl$_3$)δ:5.97(b, 2 H), 4.78(b, 2 H), 4.70(dd, J=10.6, 4.4 Hz, 1 H), 4.53(t, J=10.6 Hz, 1 H), 4.25(d, J=12.8 Hz, 1 H), 3.63(d, J=13.5 Hz, 1 H), 3.63(dd, J=11.1, 4.4 Hz, 1 H), 3.52(dd, J=12.8, 1.7 Hz, 1 H), 3.48(d, J=13.3 Hz, 1 H), 3.22(s, 3 H), 2.90(d, J=4.4 Hz, 1 H), 2.82(dd, J=4.2, 1.5 Hz, 1 H), 2.47(m, 2 H), 1.59(m, 2 H), 1.37–1.25(m, 18 H), 0.88(t, J=6.9 Hz, 3 H), 0.70(b, 1 H)

EXAMPLE 14

6-Demethyl-6-(2,3-dihydroxypropylthio)methylmitomycin C

Compound 15

Compound 15 (38 mg, yield 24%) was obtained from mg of 1a-acetyl-7-demethoxy-6-demethyl-6,7-dihydro-7-ethylenedioxy-6-methylenemitomycin A, 10 ml of chloroform and 50 mg of 3-mercapto-1,2-propanediol in a similar manner as in Example 7. Purification was carried out by preparative TLC (chloroform:methanol=8:2, v/v).

On the basis of NMR spectrum, Compound 15 was found to be a 1:1 diastereomeric mixture with asymmetric carbon on the side chain at the 6-position.

TLC : $R_f=0.19$ (CHCl$_3$:CH$_3$OH=8:2)

MS (m/z): 441 (M$^+$+1); C$_{18}$H$_{24}$N$_4$O$_7$S=440

IR (cm$^{-1}$): 3420, 2930, 1712, 1599, 1541, 1433, 1336, 1218, 1068, 853, 801, 764

NMR (400 MHz, pyridine-d$_5$)δ:8.17(b, 2 H), 7.63(b, 2 H), 5.38(dd, J=10.3, 4.2 Hz, 1 H), 5.04(b, 1 H), 4.54(d, J=12.8 Hz, 0.5 H), 4.33 (d, J=12.8 Hz, 0.5 H), 4.46 4.39 (m, 1 H), 4.16–4.04 (m, 5 H), 3.57 (bd, J=12.3 Hz, 1 H), 3.17(s, 1.5 H), 3.16(s, 1.5 H), 3.14–3.01(m, 2 H), 3.11(bs, 1 H), 2.72(bs, 1 H), 2.07(b, 1 H)

EXAMPLE 15

6-Demethyl-6-isopropylthiomethylmitomycin C (Compound 16

1a-Acetyl-7-demethoxy-6-demethyl-6,7-dihydro-7-ethylenedioxy-6-isopropylthiomethylmitomycin A [Compound (III): $R^1=CH_2OCONH_2$, $R^2=H$, $W=SCH(CH_3)_2$, $Y=CH_3$, $Z=COCH_3$, n=2] (231 mg, yield 85%) was obtained from 230 mg of 1a-acetyl-7-demethoxy-6-demethyl-6,7-dihydro-7-ethylenedioxy-6-methylenemitomycin A, 10 ml of chloroform and 50 mg of 2-propanethiol in a similar manner as in Example 7.

NMR (90 MHz, CDCl$_3$)δ:major peaks, 5.17(b, 2 H), 3.21,
3.18(s, 3 H), 2.10(s, 3 H), 1.32–1.17(m, 6 H)

Compound 16 (65 mg, yield 34%) was obtained from the above compound, 20 ml of methanol and 0.5 ml of 6.8 M ammonia/methanol solution in a similar manner as in Example 7.

TLC : R$_f$=0.42 (CHCl$_3$:CH$_3$OH=9:1)
MS (m/z): 409 (M$^+$ +1); $C_{18}H_{24}N_4O_5S$=408
IR (cm$^{-1}$): 3276, 2954, 1715, 1639, 1595, 1556, 1441, 1332, 1220, 1170, 1060, 953, 853, 820, 764, 700
NMR (400 MHz, pyridine-d$_5$)δ:8.06(b, 2 H), 7.60(b, 2 H),
5.40(dd, J=10.6, 4.4 Hz, 1 H), 5.07(t, J=10.8 Hz, 1 H), 4.57(d, J=12.8 Hz, 1 H), 4.02(dd, J=11.3, 4.4 Hz, 1 H), 3.98(d, J=13.3 Hz, 1 H), 3.82(d, J=13.3 Hz, 1 H), 3.62(dd, J=12.8, 2.0 Hz, 1 H), 3.19(s, 3 H), 3.13(d, J=4.4 Hz, 1 H), 3.00–2.93(m, 1 H), 2.74 (dd, J=4.4, 2.0 Hz, 1 H), 1.30(b, 1 H), 1.28(d, J=6.6 Hz, 3 H, 1.25(d, J=6.9 Hz, 3 H)

EXAMPLE 16

6-Demethyl-6-phenylthiomethylmitomycin C

Compound 17

1a-Acetyl-7-demethoxy-6,7-dihydro-7-ethylenedioxy-6-phenylselenomitomycin A (292 mg) was dissolved in 15 ml of chloroform, and 140 mg of potassium carbonate and 149 mg of MCPBA were added to the solution under ice cooling. After stirring at room temperature for 2 hours, the reaction mixture was poured into an aqueous sodium thiosulfate solution. The mixture was extracted with chloroform, and the chloroform layer was washed with saturated aqueous sodium chloride solution and then dried over anhydrous sodium sulfate. After the drying agent was filtered off, 0.06 ml of thiophenol was added to the filtrate, followed by stirring at room temperature for 3.5 hours. The reaction mixture was washed with an aqueous sodium bicarbonate solution and saturated aqueous sodium chloride solution, dried over anhydrous sodium sulfate, and then concentrated. The residue was subjected to silica gel column chromatography. Elution was carried out with chloroform:methanol (97:3, v/v), and reddish purple fractions were collected. The solvent was distilled off under reduced pressure to give 142 mg (yield 51%) of 1a-acetyl-7-demethoxy-6-demethyl-6,7-dihydro-7-ethylenedioxy-6-phenylthiomethylmitomycin A [Compound (III): $R^1=CH_2OCONH_2$, $R^2=H$,

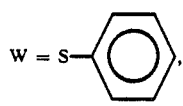

$Y=CH_3$, $Z=COCH_3$, n=2].

NMR (90 MHz, CDCl$_3$)δ:major peaks, 7.42–7.20(m, 5 H),
5.10(b, 2 H), 3.22, 3.20(s, 3 H), 2.10, 2.08(s, 3 H)

Compound 17 (27 mg, yield 29%) was obtained from 110 mg of the above compound, 25 ml of methanol and 0.3 ml of 6.8 M ammonia/methanol solution in a similar manner as in Example 7.

TLC : R$_f$=0.45 (CHCl$_3$:CH$_3$OH=9:1)
MS (m/z): 443 (M$^+$ +1); $C_{21}H_{22}N_4O_5S$=442
IR (cm$^{-1}$): 3425, 3320, 2886, 1708, 1650, 1600, 1553, 1480, 1439, 1334, 1221, 1165, 958, 852, 765, 740, 690
NMR (400 MHz, CDCl$_3$)δ:7.40–7.18(m, 5 H), 5.85(b, 2 H),
4.79(b, 2 H), 4.68(dd, J=10.6, 4.4 Hz, 1 H), 4.51 (bt, 1 H), 4.21(d, J=13.0 Hz, 1 H), 4.00(d, 12.3 Hz, 1 H), 3.89(d, J=12.6 Hz, 1 H), 3.60(dd, J=10.6, 4.4 Hz, 1 H), 3.50(bd, J=13.7 Hz, 1 H), 3.19(s, 3 H), 2.89(b, 1 H), 2.81(b, 1 H), 0.64(b, 1 H)

EXAMPLE 17

6-Demethyl-6-benzylthiomethylmitomycin C

Compound 18

Compound 18 (30 mg, yield 21%) was obtained from 184 mg of 1a-acetyl-7-demethoxy-6,7-dihydro-7-ethylenedioxy-6-phenylselenomitomycin A, 88 mg of potassium carbonate, 14 ml of chloroform, 106 mg of MCPBA and 0.05 ml of benzyl mercaptan in a similar manner as in Example 16.

TLC R$_f$=0.46 (CHCl$_3$:CH$_3$OH=9:1)
MS (m/z): 458 (M$^+$ +2); $C_{22}H_{24}N_4O_5S$=456
IR (cm$^{-1}$) 3420, 3320, 2914, 1709, 1655, 1599, 1560, 1475, 1449, 1334, 1220, 1165, 1064, 960, 852, 802, 763, 703
NMR (400 MHz, CDCl$_3$)δ:7.33–7.21(m, 5 H), 5.67(b, 2 H),
4.74(b, 2 H), 4.67(dd, J=10.8, 4.4 Hz, 1 H), 4.52 (bt, 1 H), 4.24(d, J=13.0 Hz, 1 H), 3.71(d, J=13.5 Hz, 1 H), 3.68(d, J=13.5 Hz, 1 H), 3.60(dd, J=10.6, 4.4 Hz, 1 H), 3.52(d, J=13.3 Hz, 1 H), 3.51(bd, J=13.0 Hz, 1 H), 3.47(d, J=13.3 Hz, 1 H), 3.21(s, 3 H), 2.88(b, 1 H), 2.82(b, 1 H), 0.57(b, 1 H)

EXAMPLE 18

Compound 19 [Compound (I): $R^1=CH_2OCONH_2$, $R^2=H$, $W-X=S(CH_2)_2NH$, $Y=CH_3$, $Z=COCH_3$]:

Compound 19 (55 mg, yield 23%) was obtained from 320 mg of 1a-acetyl-7-demethoxy-6,7-dihydro-7-ethylenedioxy-6-phenylselenomitomycin A, 10 ml of tetrahydrofuran, 0.7 ml of pyridine, 179 mg of MCPBA and 127 mg of 2-aminoethanethiol hydrochloride in a similar manner as in Example 2.

NMR (90 MHz, CDCl$_3$)δ:major peaks, 6.80(b, 1 H), 5.02
(b, 2 H), 3.20(s, 3 H), 2.11(s, 3 H)

EXAMPLE 19

Compound 20 [Compound (I): $R^1=CH_2OCONH_2$, $R^2=Z=H$, $W-X=S(CH_2)_2NH$, $Y=CH_3$]:

Compound 19 (55 mg) obtained in Example 18 was dissolved in 10 ml of methanol, and 0.5 ml of 6.8 M ammonia/methanol solution was added to the solution. The mixture was stirred at room temperature for 4 hours. The reaction mixture was concentrated under reduced pressure and the residue was purified by preparative TLC (chloroform:methanol=9:1, v/v) to give 33 mg (yield 66%) of Compound 20.

TLC : $R_f$=0.25 (CHCl$_3$:CH$_3$OH=9:1)
MS (m/z): 394 (M$^+$+2); C$_{17}$H$_{20}$N$_4$O$_5$S=392
IR (cm$^{-1}$): 3440, 3310, 2930, 1711, 1633, 1600, 1554, 1507, 1452, 1338, 1202, 1152, 1070, 960, 847, 806, 756, 705
NMR (400 MHz, CDCl$_3$)δ:6.70(b, 1 H), 4.82(b, 2 H), 4.68
(dd, J=10.6, 4.4 Hz, 1 H), 4.49(t, J=10.6 Hz, 1 H), 4.27(d, J=13.0 Hz, 1 H), 3.91(bt, J=5.4 Hz, 2 H), 3.87(d, J=16.2 Hz, 1 H), 3.82(d, J=16.2 Hz, 1 H), 3.60(dd, J=10.6, 4.4 Hz, 1 H), 3.51(dd, J=13.0, 1.7 Hz, 1 H), 3.20(s, 3 H), 3.08(bt, J=5.4 Hz, 2 H), 2.90 (d, J=4.4 Hz, 1 H), 2.82(dd, J=4.4, 1.7 Hz, 1 H), 0.90(b, 1 H)

EXAMPLE 20

6-Demethyl-6-allyloxymethylmitomycin C

Compound 21

1a-Acetyl-7-demethoxy-6-demethyl-6,7-dihydro-7-ethylenedioxy-6-allyloxymethylmitomycin A [Compound (III): R$^1$=CH$_2$OCONH$_2$, R$^2$=H, W=OCH$_2$CH=CH$_2$, Y=CH$_3$, Z=COCH$_3$, n=2] (49.2 mg, yield 42%) was obtained from 102 mg of 1a-acetyl-7-demethoxy-6-demethyl-6,7-dihydro-7-ethylenedioxy-6-methylenemitomycin A, 5.0 ml of allyl alcohol and 5.0 μl of Triton B (40% aqueous solution) in a similar manner as in Example 7.

Compound 21 (16.4 mg, yield 41%) was obtained as purple powder from 49.2 mg of the above compound, 5.0 ml of methanol and 0.50 ml of 6.1 M ammonia/methanol solution in a similar manner as in Example 7.

TLC : $R_f$=0.39 (CHCl$_3$:CH$_3$OH=9:1)
MS (m/z): 391 (M$^+$+1); C$_{18}$H$_{22}$N$_4$O$_6$=390
IR (cm$^{-1}$): 3430, 3320, 3200, 2930, 1710, 1600, 1550, 1450, 1400, 1340, 1210, 1060
NMR (270 MHz, pyridine-d$_5$)δ:8.3–7.9(br, 2 H), 7.9–7.4
(br, 2 H), 5.95(m, 1 H), 5.42(dd, J=4.2, 10.3 Hz, 1 H), 5.30(ddd, J=17.4, 3.7, 1.8 Hz, 1 H), 5.2–5.0
(m, 1 H), 5.09(ddd, J=10.4, 3.3, 1.5 Hz, 1 H), 4.71
(d, J=11.7 Hz, 1 H), 4.64(d, J=12.6 Hz, 1 H), 4.57(d, J=12.6 Hz, 1 H), 4.04(dd, J=11.2, 4.2 Hz, 1 H), 3.97
(m, 2 H), 3.60(d, J=12.8 Hz, 1 H), 3.20(s, 3 H), 3.18
(bs, 1 H), 2.75(bs, 1 H), 2.15(bs, 1 H)

EXAMPLE 21

6-Demethyl-6-(2-methoxyethoxy)methylmitomycin C

Compound 22

1a-Acetyl-7-demethoxy-6-demethyl-6,7-dihydro-7-ethylenedioxy-6-(2-methoxyethoxy)methylmitomycin A [Compound (III): R$^1$=CH$_2$OCONH$_2$, R$^2$=H, W=OCH$_2$CH$_2$OCH$_3$, Y=CH$_3$, Z=COCH$_3$, n=2] (61.8 mg, yield 17%) was obtained from 210 mg of 1a-acetyl-7-demethoxy-6-demethyl-6,7-dihydro-7-ethylenedioxy-6-methylenemitomycin A, 30 ml of 2-methoxyethanol and 10 μl of Triton B (40% aqueous solution) in a similar manner as in Example 7.

The obtained compound (61.8 mg) was dissolved in 20 ml of anhydrous tetrahydrofuran. The solution was allowed to stand at room temperature for 7 days in an ammonia gas atmosphere. After the solvent was distilled off under reduced pressure, the residue was subjected to post-treatment and purification in a similar manner as in Example 7 to give 4.3 mg (yield 8.4%) of Compound 22 as purple powder.

TLC : $R_f$=0.25 (CHCl$_3$:CH$_3$OH=9:1)
MS (m/z): 409 (M$^+$+1); C$_{18}$H$_{24}$N$_4$O$_7$=408
IR (cm$^{-1}$): 3410, 3300, 3200, 2920, 1710, 1600, 1550, 1450, 1340, 1070
NMR (90 MHz, pyridine-d$_5$)δ:major peaks, 8.1–7.0(br,
4 H), 5.32(dd, J=11, 4 Hz, 1 H), 4.97(t, J=11 Hz, 1 H),
4.64(bs, 2 H), 4.50(d, J=13 Hz, 1 H), 3.94(dd, J=11, 4 Hz, 1 H), 3.7–3.3(m, 5 H), 3.24(s, 3 H), 3.19 (s, 3 H)

EXAMPLE 22

6-Demethyl-6-[(4-hydroxyphenyl)thio]methylmitomycin C

Compound 23

1a-Acetyl-7-demethoxy-6-demethyl-6,7-dihydro-7-ethylenedioxy-6-[(4-hydroxyphenyl)thio]methylmitomycin A [Compound (III): R$^1$=CH$_2$OCONH$_2$, R$_2$=H,

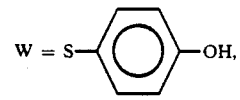

Y=CH$_3$, Z=COCH$_3$, n=2] (190 mg, yield 68%) was obtained from 297 mg of 1a-acetyl-7-demethoxy-6,7-dihydro-6-phenylselenomitomycin A, 161 mg of MCPBA, 25 ml of chloroform and 120 μl of 4-hydroxythiophenol in a similar manner as in Example 2.

The obtained compound (154 mg) was dissolved in 20 ml of methanol, and 400 mg of ammonium acetate was added to the solution. The mixture was stirred at room temperature for 9 hours and then diluted with chloroform. The diluted mixture was washed with saturated aqueous sodium chloride solution three times and dried over anhydrous sodium sulfate. After the solvent was distilled off under reduced pressure, the residue was subjected to purification and drying in a similar manner as in Example 7 to give 37.8 mg (yield 29%) of Compound 23 as grayish green powder.

TLC : $R_f$=0.32 (CHCl$_3$:CH$_3$OH=9:1)
MS (m/z): 460 (M$^+$+2); C$_{21}$H$_{22}$N$_4$O$_5$S=458
IR (cm$^{-1}$): 3450, 3370, 2950, 1710, 1660, 1580, 1500, 1340, 1270, 1080, 1040
NMR (270 MHz, pyridine-d$_5$)δ:12–11(br, 1 H), 8.3–8.0
(br, 2 H), 7.9–7.3(br, 2 H), 7.6–7.5(m, 2 H), 7.1–7.0 (m, 2 H), 5.42(dd, J=10.4, 4.3 Hz, 1 H), 5.11(bt, J=11.2 Hz, 1 H), 4.49(d, J=12.7 Hz, 1 H), 4.35(d, J=12.2 Hz, 1 H), 4.25(d, J=12.0 Hz, 1 H), 4.02(dd, J=11.2, 4.2 Hz, 1 H), 3.54(bd, J=13.4 Hz, 1 H), 3.17(s, 3 H), 3.13(bs, 1 H), 2.71(bs, 1 H), 2.09(bt, J=7.1 Hz, 1 H)

EXAMPLE 23

6-Demethyl-6-[(4-chlorophenyl)thio]methylmitomycin C

Compound 24

1a-Acetyl-7-demethoxy-6-demethyl-6,7-dihydro-7-ethylenedioxy-6-[(4-chlorophenyl)thio]methylmitomycin A [Compound (III): R$^1$=CH$_2$OCONH$_2$, R$^2$=H,

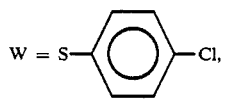

Y=CH₃, Z=COCH₃,n=2] (184 mg, yield 62%) was obtained from 219 mg of la-acetyl-7-demethoxy-6-demethyl-6,7-dihydro-7-ethylenedioxy-6-methylenemitomycin A, 153 mg of 4-chlorothiophenol, 0.15 ml of triethylamine and 50 ml of chloroform in a similar manner as in Example 7.

Compound 24 (34.3 mg, yield 36%) was obtained as purple powder from 114 mg of the above compound, 30 ml of methanol and 1.1 ml of 6.1 M ammonia/methanol solution in a similar manner as in Example 7.

TLC : $R_f$=0.31 (CHCl₃:CH₃OH=9:1)

MS (m/z): 477, 479 (M⁺+1); $C_{21}H_{21}ClN_4O_5S$ =476.5

IR (cm⁻¹): 3420, 3320, 3220, 2930, 1710, 1600, 1550, 1470, 1450, 1340, 1220, 1070

NMR (90 MHz, pyridine-d₅)δ:8.4–7.8(br, 4 H), 7.6–7.0

(m, 4 H), 5.27(dd, J=10, 4 Hz, 1 H), 4.93(t, J=11 Hz, 1 H), 4.40(d, J=13 Hz, 1 H), 4.22(bs, 2 H), 3.91(dd, J=11, 5 Hz, 1 H), 3.49(d, J=13 Hz, 1 H), 3.19(s, 3 H), 3.05(bs, 1 H), 2.70(bs, 1 H), 1.8(bs, 1 H)

EXAMPLE 24

6-Demethyl-6[(4-methoxyphenyl)thio]methylmitomycin C

Compound 25 la-Acetyl-7-demethoxy-6-demethyl-6,7-dihydro-7-ethylenedioxy-6-[(4-methoxyphenyl)thio]methylmitomycin A [Compound (III): R=CH₂OCONH₂, R²=H,

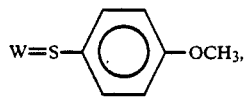

Y=CH₃, Z=COCH₃, n=2] (186 mg, yield 63%) was obtained from 219 mg of la-acetyl-7-demethoxy-6-demethyl-6,7-dihydro-7-ethylenedioxy-6-methylenemitomycin A, 134 mg of 4-methoxythiophenol, 0.15 ml of triethylamine and 50 ml of chloroform in a similar manner as in Example 7.

Compound 25 (47.4 mg, yield 37%) was obtained as purple powder from 154 mg of the above compound, 15 ml of methanol and 1.0 ml of 6.1 M ammonia/methanol solution in a similar manner as in Example 7.

TLC : $R_f$=0.49 (CHCl₃:CH₃OH=9:1)

MS (m/z) 473 (M⁺+1); $C_{22}H_{24}N_4O_6S$=472

IR (cm⁻¹): 3420, 3310, 3200, 2920, 1710, 1590, 1490, 1440, 1330, 1240, 1070

NMR (270 MHz, pyridine-d₅)δ:8.4–8.1(br, 2 H), 7.9–7.4

(br, 2 H), 7.6–7.5(m, 2 H), 6.9–6.8(m, 2 H), 5.42

(dd, J=10.4, 4.2 Hz, 1 H), 5.09(bt, J=10.2 Hz, 1 H), 4.45(d, J=12.6 Hz, 1 H), 4.32(d, J=12.1 Hz, 1 H), 4.26(d, J=11.9 Hz, 1 H), 4.02(dd, J=11.2, 4.2 Hz, 1 H), 3.61(s, 3 H), 3.55(d, J=12.1 Hz, 1 H), 3.18(s, 3 H), 3.12(bs, 1 H), 2.72(bs, 1 H), 2.12(br, 1 H)

EXAMPLE 25

6-Demethyl-6-[(4-nitrophenyl)thio]methylmitomycin C

Compound 26 la-Acetyl-7-demethoxy-6-demethyl-6,7-dihydro-7-ethylenedioxy-6-[(4-nitrophenyl)thio]methylmitomycin A [Compound (III): R¹=CH₂OCONH₂, R²=H,

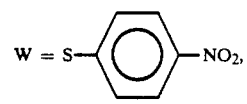

Y=CH₃, Z=COCH₃, n=2] (289 mg, yield 68%) was obtained from 311 mg of la-acetyl-7-demethoxy-6-demethyl-6,7-dihydro-7-ethylenedioxy-6-methylenemitomycin A, 145 mg of 4-nitrothiophenol (purity 80%), 0.10 ml of triethylamine and 30 ml of dichloromethane in a similar manner as in Example 7.

Compound 26 (7.7 mg, yield 4%) was obtained as gray powder from 225 mg of the above compound, 20 ml of anhydrous tetrahydrofuran and ammonia gas in a similar manner as in Example 21.

TLC : $R_f$=0.34 (CHCl₃:CH₃OH=9:1)

MS (m/z): 488 (M⁺+1); $C_{21}H_{21}N_5O_7S$=487

IR (cm⁻¹): 3420, 3320, 3200, 2920, 1710, 1590, 1550, 1500, 1470, 1440, 1330, 1220, 1070

NMR (270 MHz, pyridine-d₅)δ:8.03(dd, J=7.1, 1.9 Hz,

2 H), 7.9–7.4(br, 4 H), 7.33(dd, J=7.1, 1.9 Hz, 2 H), 5.44(dd, J=10.3, 4.2 Hz, 1 H), 5.11(bt, J=12 Hz, 1 H), 4.58(d, J=12.8 Hz, 1 H), 4.43(d, J=11.5 Hz, 1 H), 4.34(d, J=11.5 Hz, 1 H), 4.06(dd, J=11.1, 4.1 Hz, 1 H), 3.62(d, J=11.4 Hz, 1 H), 3.21(s, 3 H), 3.15(bs, 1 H), 2.77(bs, 1 H), 2.17(br, 1 H)

EXAMPLE 26

Compound 27 [Compound (I): R¹=CH₂OCONH₂, R²=H, W—X=

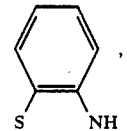

Y=CH₃, Z=COCH₃]:

Compound 27 (146 mg, yield 42%) was obtained as green powder from 299 mg of la-acetyl-7-demethoxy-6-demethyl-6,7-dihydro-7-ethylenedioxy-6-methylenemitomycin A, 90 mg of 2-aminothiophenol, 0.10 ml of triethylamine and 30 ml of dichloromethane in a similar manner as in Example 7.

TLC : $R_f$=0.59 (CHCl₃:CH₃OH=9:1)

NMR (90 MHz, CDCl₃)δ:major peaks, 8.94(bs, 1 H), 7.6–6.9(m, 4 H), 3.25(s, 3 H), 2.13(s, 3 H)

EXAMPLE 27

Compound 28 [Compound (I): R¹=CH₂OCONH₂, R²=H, W—X=

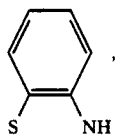

Y=CH$_3$, Z=H]:

Compound 27 (123 mg) obtained in Example 26 was dissolved in 50 ml of methanol, and 11 mg of potassium carbonate was added to the solution, followed by stirring at room temperature for 3 hours and 20 minutes. The reaction mixture was neutralized with phosphate buffer, pH 4, and extracted with chloroform. By post-treatment, purification and drying in a similar manner as in Example 22, 75.9 mg (yield 57%) of Compound 28 was obtained as green powder.

TLC : R$_f$=0.52 (CHCl$_3$:CH$_3$OH=9:1)

MS (m/z): 441 (M$^+$+1); C$_{21}$H$_{20}$N$_4$O$_5$S=440

IR (cm$^{-1}$) 3450, 3350, 3300, 3200, 2920, 1710, 1640, 1570, 1520, 1480, 1330, 1240, 1150, 1070

NMR (270 MHz, pyridine-d$_5$)δ:9.35(s, 1 H), 8.0–7.4(br,

2 H), 7.48(dd, J=7.7, 1.5 Hz, 1 H), 7.36(dd, J=7.1, 1.1 Hz, 1 H), 7.26(dt, J=7.2, 1.4 Hz, 1 H), 7.03(dt, J=7.4, 1.4 Hz, 1 H), 5.37(dd, J=10.4, 4.2 Hz, 1 H), 5.10(t, J=10.8 Hz, 1 H), 4.45(d, J=12.8 Hz, 1 H), 4.19(d, J=15.6 Hz, 1 H), 4.03(dd, J=11.3, 4.3 Hz, 1 H), 3.84(d, J=15.4 Hz, 1 H), 3.59(d, J=12.8 Hz, 1 H), 3.23(s, 3 H), 3.16(bs, 1 H), 2.78(bs, 1 H), 2.22(bt, 1 H)

EXAMPLE 28

6-Demethyl-6-cyclopropylmethylthiomethylmitomycin C

Compound 29 la-Acetyl-7-demethoxy-6-demethyl-6,7-dihydro-7-ethylenedioxy-6-cyclopropylmethylthiomethylmitomycin A [Compound (III): R$^1$=CH$_2$OCONH$_2$, R$^2$=H,

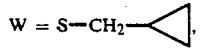

Y=CH$_3$, Z=COCH$_3$] (204 mg, yield 56%) was obtained from 300 mg of la-acetyl-7-demethoxy-6-demethyl-6,7-dihydro-7-ethylenedioxy-6-methylenemitomycin A, 100 μl of cyclopropylmethanethiol and 30 ml of dichloromethane in a similar manner as in Example 7.

Compound 29 (73.6 mg, yield 44%) was obtained as purple powder from 204 mg of the above compound, 30 ml of anhydrous tetrahydrofuran and ammonia gas in a similar manner as in Example 21.

TLC : R$_f$=0.34 (CHCl$_3$CH$_3$OH=9:1)

MS (m/z): 421 (M$^+$+1); C$_{19}$H$_{24}$N$_4$O$_5$S=420

IR (cm$^{-1}$) 3430, 3310, 3200, 2920, 1710, 1590, 1550, 1440, 1330, 1220, 1070

NMR (270 MHz, pyridine-d$_5$)δ:8.3–8.0(br, 2 H), 7.9–7.4

(br, 2 H), 5.42(dd, J=10.4, 4.2 Hz, 1 H), 5.10(bt, 1 H), 4.57(d, J=12.8 Hz, 1 H), 4.04(d, J=12.8 Hz, 1 H), 4.03(dd, J=11.0, 4.9 Hz, 1 H), 3.86(d, J=13.0 Hz, 1 H), 3.61(d, J=11.9 Hz, 1 H), 3.19(s, 3 H), 3.14(bs, 1 H), 2.74(bs, 1 H), 2.60(dd, J=13.0, 7.0 Hz, 1 H), 2.52(dd, J=12.9, 7.1 Hz, 1 H), 2.14(br, 1 H), 1.10 (m, 1 H), 0.43(m, 2 H), 0.18(m, 2 H)

REFERENCE EXAMPLE 1 la-Acetyl-7-demethoxy-6,7-dihydro-7-ethylenedioxymitomycin A [Compound (V): R$^1$=CH$_2$OCONH$_2$, R$^2$=H, Y=CH$_3$, Z=COCH$_3$, n=2]:

Mitomycin A (1.0 g) was dissolved in 15 ml of tetrahydrofuran and 3 ml of ethylene glycol, and 0.5 ml of 1.6% (w/w) solution of potassium hydroxide in ethylene glycol was added to the solution. The mixture was stirred at 25° C. for 5 hours, followed by addition of excess dry ice in small pieces. After stirring, the reaction mixture was diluted with chloroform. The organic layer was washed with saturated aqueous sodium chloride solution and dried over anhydrous sodium sulfate. The solvent was distilled off under reduced pressure and the residue was subjected to silica gel column chromatography. Elution was carried out with chloroform:methanol (97:3, v/v), and yellowish orange fractions were collected. After the solvent was distilled off under reduced pressure, the residue was dissolved in a small quantity of chloroform and n-hexane was added to the solution to give powder. Then, the solvent was distilled off under reduced pressure. The residue was thoroughly dried in vacuo at 25° C. to give 880 mg (yield 81%) of 7-demethoxy-6,7-dihydro-7-ethylenedioxymitomycin A as yellowish orange powder.

TLC : R$_f$=0.27(CHCl$_3$:CH$_3$OH=9:1)

MS (m/z): 380 (M$^+$+1); C$_{17}$H$_{21}$N$_3$O$_7$=379

IR (cm$^{-1}$); 3446, 3296, 2902, 1727, 1702, 1642, 1575, 1447, 1336, 1186, 1068, 964, 855, 757, 705

NMR (400 MHz, CDCl$_3$)δ:0.90(bs, 1 H), 1.18(d, J=6.6 Hz,

3 H), 2.80(bs, 1 H), 2.91(d, J=4.2 Hz, 1 H), 3.21(s, 3 H), 3.27(q, J=6.6 Hz, 1 H), 3.44(dd, J=12.3, 1.5 Hz, 1 H), 3.62(dd, J=10.6, 4.4 Hz, 1 H), 3.83(d, J=12.8 Hz, 1 H), 3.98–4.13(m, 3 H), 4.39(m, 1 H), 4.58 (t, J=10.6 Hz, 1 H), 4.78(dd, J=10.6, 4.4 Hz, 1 H), 4.80(bs, 2 H)

The above compound (52 mg) was dissolved in 1.0 ml of chloroform and 0.5 ml of pyridine, and 13 μl of acetic anhydride was added to the solution. After stirring at 25° C. for one hour, 1.0 ml of methanol was added to the mixture, followed by stirring for 10 minutes. Then, 2 ml of toluene was added to the reaction mixture and the solvent was distilled off under reduced pressure. The residue was subjected to silica gel column chromatography. Elution was carried out with chloroform:methanol (96:4, v/v), and yellow fractions were collected. After the solvent was distilled off under reduced pressure, the residue was treated in a similar manner as above to give 53 mg (yield 95%) of the desired compound as yellow powder.

From the NMR spectrum, the obtained compound was found to be a diastereomeric mixture of about 2.5:1 having different stereochemistry at the C$_6$-position.

TLC : R$_f$0.52 (CHCl$_3$:CH$_3$OH=9:1)

MS (m/z): 422 (M$^+$+1); C$_{19}$H$_{23}$N$_3$O$_8$=421

IR (cm$^{-1}$): 3480, 3292, 2900, 1720, 1700, 1645, 1575, 1448, 1328, 1268, 1189, 1067, 1031, 949, 859, 749

NMR (400 MHz, CDCl$_3$)δ:

Major: 120(d, J=6.6 Hz, 3 H), 2.11(s, 3 H), 3.21(s, 3 H), 3.22(q, J=6.6 Hz, 1 H), 3.23(dd, J=4.4, 2.0 Hz, 1 H), 3.47(dd, J=13.1, 2.0 Hz, 1 H), 3.50(d, J=4.4 Hz, 1 H), 3.73(dd, J=10.8, 4.9 Hz, 1 H), 4.04(d, J=13.1 Hz, 1 H), 3.98–4.41(m, 4 H), 4.17(t, J=11.1 Hz, 1 H), 4.82(bs, 2 H), 4.98(dd, J=11.1, 4.9 Hz, 1 H)

Minor: major peaks 1.24(d, J=6.9 Hz, 3 H), 2.11(s, 3 H), 3.04 (q, J=6.9

Hz, 1 H), 3.22(s, 3 H), 3.42(dd, J=13.0, 1.7 Hz, 1 H), 4.34(d, J=13.0 Hz, 1 H), 4.89(dd, J=10.8, 4.9 Hz, 1 H)

REFERENCE EXAMPLE 2

1a-Acetyl-7-demethoxy-6,7-dihydro-7-ethylenedioxy-6-phenylselenomitomycin A [Compound (VI): $R^1=CH_2OCONH_2$, $R^2=H$, $Y=CH_3$, $Z=COCH_3$, n=2]:

1a-Acetyl-7-demethoxy-6,7-dihydro-7-ethylenedioxymitomycin A (120 mg) was dissolved in 4.0 ml of tetrahydrofuran, and 0.3 ml of triethylamine was added to the solution. After stirring at 25° C. for 30 minutes, 67 mg of phenylselenenyl bromide was added to the mixture. The mixture was stirred at 25° C. for 30 minutes and 60 mg of phenylselenenyl bromide was further added. After stirring for 20 minutes, the solvent was distilled off under reduced pressure and the residue was subjected to silica gel column chromatography. Elution was carried out with chloroform:methanol (97:3, v/v), and yellow fractions were collected. After the solvent was distilled off under reduced pressure, the residue was treated in a similar manner as in Reference Example 1 to give 149 mg (yield 91%) of the desired compound as yellow powder.

From the NMR spectrum, the obtained compound was found to be a diastereomeric mixture of about 2:1 having different stereochemistry at the $C_6$-position.

TLC: $R_f=0.49$ ($CHCl_3:CH_3OH=9:1$)
MS (m/z): 578 (M++2); $C_{25}H_{27}N_3O_8Se=576$
IR (cm$^{-1}$): 3460, 2970, 1725, 1688, 1656, 1571, 1435, 1377, 1334, 1247, 1205, 1066, 1031, 987, 857, 742
NMR (400 MHz, CDCl$_3$)δ:
Major: 145(s, 3 H), 2.18(s, 3 H), 3.16(s, 3 H) 3.27(dd, J=4.7, 2.0 Hz, 1 H), 3.39(dd, J=13.0, 2.0 Hz, 1 H), 3.51(d, J=4.4 Hz, 1 H), 3.80dd, J=11.3, 4.9 Hz, 1 H), 3.84(d, J=13.0 Hz, 1 H), 3.95–4.50 (m, 4 H), 4.28(t, J=11.1 Hz, 1 H), 5.15(dd, J=11.0, 4.7 Hz, 1 H), 5.80(bs, 2 H), 7.24–7.63(m, 5 H)
Minor: major peaks
1.42(s, 3H), 2.18(s, 3 H), 3.22(dd, J=4.4, 2.0 Hz, 1 H), 3.26(s, 3 H), 3.38(dd, J=13.0, 2.2 Hz, 1 H), 3.47(d, J=4.4 Hz, 1 H), 3.75(dd, J=11.0, 4.7 Hz, 1 H), 4.14(t, J=10.8 Hz, 1 H), 4.54(d, J=12.9 Hz, 1 H), 4.85(dd, J=11.0, 4.7 Hz, 1 H)

REFERENCE EXAMPLE 3

1a-Acetyl-7-demethoxy-6-demethyl-6,7-dihydro-7-ehtylenedioxy-6-methylenemitomycin A [Compound (II): $R^1=CH_2OCONH_2$, $R^2=H$, $Y=CH_3$, $Z=COCH_3$, n=2]:

1a-Acetyl-7-demethoxy-6,7-dihydro-7-ethylenedioxy-6-phenylselenomitomycin A (833 mg) was dissolved in 30 ml of chloroform, and 380 mg of potassium carbonate was added to the solution. The mixture was cooled to 0° C. and 17 ml of a solution of 425 mg of MCPBA in chloroform was added dropwise thereto over 40 minutes. After stirring at room temperature for 50 minutes, the reaction mixture was poured into an aqueous solution mixture of sodium thiosulfate and sodium bicarbonate. The resulting mixture was extracted with chloroform. The chloroform layer was washed with saturated aqueous sodium chloride solution and then dried over anhydrous sodium sulfate, followed by addition of n-hexane to give powder. The solvent was distilled off under reduced pressure and the residue was thoroughly dried in vacuo to give 590 mg (yield 97%) of the desired compound as yellow powder.

TLC: $R_f=0.52$ ($CHCl_3:CH_3OH=9:1$)
MS (m/z): 420 (M++1); $C_{19}H_{21}N_3O_8=419$
IR (cm$^{-1}$) 3470, 3370, 2950, 1702, 1658, 1571, 1458, 1383, 1333, 1269, 1110, 1057, 1025, 984, 948, 861, 801, 709
NMR (400 MHz, CDCl$_3$)δ:6.39(d, J=1.2 Hz, 1 H), 6.11(d, J=1.2 Hz, 1 H), 4.92(dd, J=10.8, 4.7 Hz, 1 H), 4.77 (b, 2 H), 4.39(d, J=13.0 Hz, 1 H), 4.32–4.08(m, 4 H), 4.15(t, J=10.8 Hz, 1 H), 3.75(dd, J=10.8, 4.9 Hz, 1 H), 3.52(dd, J=13.3, 2.0 Hz, 1 H), 3.51(d, J=4.4 Hz, 1 H), 3.24(dd, J=4.4, 2.0 Hz, 1 H), 3.22(s, 3 H), 2.12(s, 3 H)

What is claimed is:

1. A mitomycin derivative represented by the formula:

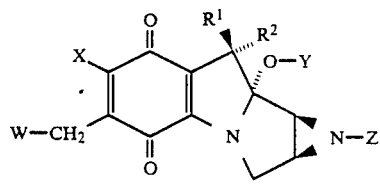

wherein W represents RO or RS (wherein R represents hydrogen; alkyl having 1 to 12 carbon atoms which may be substituted with 1 or 2 substituents independently selected from the group consisting of hydroxy, lower alkoxy having 1 to 4 carbon atoms, lower alkoxycarbonyl having 2 to 5 carbon atoms and alicyclic alkyl having 3 to 6 carbon atoms; alkenyl having 2 to 12 carbon atoms; a substituted or non-substituted aralkyl selected from the group consisting of benzyl, phenethyl and benzhydryl; or a substituted or non-substituted aryl selected from the group consisting of phenyl and naphthyl; substituents for said substituted aralkyl and for said substituted aryl being 1 to 3 substituents independently selected from the group consisting of hydroxy, lower alkoxy having 1 to 4 carbon atoms, halogen, nitro and lower alkyl having 1 to 4 carbon atoms; X represents methoxy or amino; or W and X are combined together to form —S(CH$_2$)$_2$NH— or

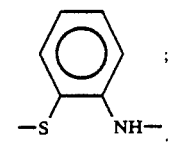

Y represents hydrogen or methyl; Z represents hydrogen, methyl or lower alkanoyl having 1 to 4 carbon atoms; and one of $R^1$ and $R^2$ represents carbamoyloxymethyl and the other represents hydrogen.

2. A mitomycin derivative according to claim 1, wherein said alkyl having 1 to 12 carbon atoms is a straight-chain or branched alkyl group and is selected from the group consisting of methyl, ethyl, propyl, isopropyl, butyl, isobutyl, tert-butyl, pentyl, hexyl, heptyl, octyl, decyl and dodecyl.

3. A mitomycin derivative according to claim 1, wherein said alkenyl having 2 to 12 carbon atoms is selected from the group consisting of vinyl, allyl, homoallyl, crotyl and cis-7-dodecenyl.

* * * * *